US005945127A

United States Patent [19]

Breitenbach et al.

[11] Patent Number: 5,945,127

[45] Date of Patent: Aug. 31, 1999

[54] STORAGE-STABLE DRUG FORM

[75] Inventors: Jörg Breitenbach, Mannheim; Jens Rieger, Ludwigshafen; Joerg Rosenberg, Ellerstadt; Axel Sanner, Frankenthal, all of Germany

[73] Assignee: BASF Aktiengesellschaft, Ludwigshafen, Germany

[21] Appl. No.: 08/913,513

[22] PCT Filed: Mar. 9, 1996

[86] PCT No.: PCT/EP96/01019

§ 371 Date: Sep. 16, 1997

§ 102(e) Date: Sep. 16, 1997

[87] PCT Pub. No.: WO96/29060

PCT Pub. Date: Sep. 26, 1996

[30] Foreign Application Priority Data

Mar. 21, 1995 [DE] Germany ........................... 195 09 806

[51] Int. Cl.$^{6}$ ........................................ A61K 9/14

[52] U.S. Cl. ........................... 424/489; 424/465; 424/488

[58] Field of Search .................................... 424/489, 465, 424/488

[56] References Cited

U.S. PATENT DOCUMENTS

| | | | |
|---|---|---|---|
| 4,520,180 | 5/1985 | Barabas et al. | 526/212 |
| 4,801,460 | 1/1989 | Goertz et al. | 424/465 |

FOREIGN PATENT DOCUMENTS

| | | |
|---|---|---|
| 0240904B1 | 1/1992 | Germany . |

*Primary Examiner*—Thurman K. Page
*Assistant Examiner*—William E. Benston, Jr.
*Attorney, Agent, or Firm*—Keil & Weinkauf

[57] ABSTRACT

Solid drug forms obtainable by extrusion of a melt comprising, besides one or more active substances, a mixture of homo- and/or copolymers of N-vinylpyrrolidone and degraded starches.

5 Claims, No Drawings

STORAGE-STABLE DRUG FORM

This application is a 371 of PCT/EQ96/01019 Mar. 9, 1996.

The present invention relates to solid drug forms obtainable by extrusion of a solvent-free melt comprising, besides one or more active substances, a mixture of a) 10–99% by weight of one or more water-soluble, melt-processable, homo- or copolymers of N-vinylpyrrolidone, b) 1–90% by weight of degraded starches, and c) 0–50% by weight of one or more conventional pharmaceutical ancillary substances, and subsequent shaping.

The production of solid drug forms by extrusion of a melt comprising, besides the active substance, polymers based on N-vinylpyrrolidone, with subsequent shaping, is disclosed, for example, in EP-B 240 904.

WO 93/10758 describes slow-release drug forms based on an amorphous carbohydrate glass matrix which contain polyvinylpyrrolidone or maltodextrins as agents for recrystallization. To produce the matrix, aqueous solutions of the matrix components are heated until viscous mixtures are obtained, and the active substance is incorporated therein by kneading, after which the active substance-containing mixture can be processed for example by extrusion.

A fundamental difficulty in the production of solid drug forms by extrusion of active substance-containing melts is that the polymers used for matrix formation must, on the one hand, have adequate melt-processability but, on the other hand, remain dimensionally stable in the finished drug form even on prolonged storage. Polymers with good melt-processability are, in particular, those which either have relatively low molecular weights and thus relatively low glass transition temperatures and/or contain plasticizing monomers such as vinyl acetate, ie. precisely these polymers result in the unwanted phenomenon of cold flow on processing to solid drug forms.

It is an object of the present invention to find storage-stable solid drug forms which are obtainable in a simple manner by extrusion of active substance-containing melts and subsequent shaping.

We have found that this object is achieved by the drug forms defined at the outset.

Examples of suitable active substances are:

betamethasone, thioctic acid, sotalol, salbutamol, norfenefrine, silymarin, dihydroergotamine, buflomedil, etofibrate, indometacin, oxazepam, beta-acetyldigoxin, piroxicam, haloperidol, ISMN, amitriptyline, diclofenac, nifedipine, verapamil, pyritinol, nitrendipine, doxycycline, bromhexine, methylprednisolone, clonidine, fenofibrate, allopurinol, pirenzepine, levothyroxine, tamoxifen, metildigoxin, o-(beta-hydroxyethyl)rutoside, propicillin, aciclovir mononitrate, paracetamol, naftidrofuryl, pentoxyfylline, propafenone, acebutolol, L-thyroxine, tramadol, bromocriptine, loperamide, ketotifen, fenoterol, Ca dobesilate, propranolol, minocycline, nicergoline, ambroxol, metoprolol, beta-sitosterol, enalapril hydrogen maleate, bezafibrate, ISDN, gallopamil, xantinol nicotinate, digitoxin, flunitrazepam, bencyclane, dexpanthenol, pindolol, lorazepam, diltiazem, piracetam, phenoxymethylpenicillin, furosemide, bromazepam, flunarizine, erythromycin, metoclopramide, acemetacin, ranitidine, biperiden, metamizole, doxepin, dipotassium chlorazepate, tetrazepam, estramustine phosphate, terbutaline, captopril, maprotiline, prazosin, atenolol, glibenclamide, cefaclor, etilefrine, cimetidine, theophylline, hydromorphone, ibuprofen, primidone, clobazam, oxaceprol, medroxyprogesterone, flecainide, Mg pyridoxal-5-phosphate glutamate, hymechromone, etofylline clofibrate, vincamine, cinnarizine, diazepam, ketoprofen, flupentixol, molsidomine, glibornuride, dimethindene, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, myrtol, bromelaines, prenylamine, salazosulfapyridine, astemizole, sulpiride, benserazide, dibenzepine, acetylsalicylic acid, miconazole, nystatin, ketoconazole, Na picosulfate, colestyramine, gemfibrozil, rifampicin, fluocortolone, mexiletine, amoxicillin, terfenadine, mucopolysaccharide polysulfates, triazolam, mianserin, tiaprofenic acid, amezinium metilsulfate, mefloquine, probucol, quinidine, carbamazepine, Mg L-aspartate, penbutolol, piretanide, amitriptyline, cyproterone, Na valproate, mebeverine, bisacodyl, 5-aminosalicylic acid, dihydralazine, magaldrate, phenprocoumon, amantadine, naproxen, carteolol, famotidine, methyldopa, auranofin, estriol, nadolol, levomepromazine, doxorubicin, metofenazate, azathioprine, flutamide, norfloxacin, fendiline, prajmalium bitartrate, escin.

Acetaminophen (=paracetamol), acetohexamide, acetyldigoxin, acetylsalicylic acid, acromycin, anipamil, benzocaine, beta-carotene, chloramphenicol, chlordiazepoxide, chlormadinone acetate, chlorthiazide, cinnarizine, clonazepam, codeine, dexamethasone, diazepam, dicumarol, digitoxin, digoxin, dihydroergotamine, drotaverine, flunitrazepam, furosemide, gramicidin, griseofulvin, hexobarbital, hydrochlorothiazide, hydrocortisone, hydroflumethazide, ibuprofen, indometacin, ketoprofen, lonetil, medazepam, mefruside, methandrostenolone, methylprednisolone, methylsulfadiazine (=sulfaperin), nalidixic acid, nifedipin, nitrazepam, nitrofurantoin, nystatin, estradiol, papaverine, phenacetin, phenobarbital, phenylbutazone, phenytoin, prednisone, reserpine, spironolactone, streptomycin, sulfadimidine (=sulfamethazine), sulfamethizole, sulfamethoxazole (=sulfameter), sulfaperin, sulfathiazole, sulfisoxazole, testosterone, tolazamide, tolbutamide, trimethoprim, tyrothricin.

Vitamins can also be formulated according to the invention. These include vitamins of the A group, the B group, including not only B1, B2, B6 and B12, and nicotinic acid and nicotinamide, but also compounds with vitamin B properties such as adenine, choline, pantothenic acid, biotin, adenylic acid, folic acid, orotic acid, pangamic acid, carnitine, p-aminobenzoic acid, myo-inositol and α-lipoic acid. Furthermore vitamines of the C group, D group, E group, F group, H group, I and J group, K group and P group.

Very particularly preferred active substances according to the invention are ibuprofen, acetylsalicylic acid, paracetamol, phenazone, flurbiprofen, captopril, nifedipine, acetylcysteine, naftidrofuryl, verapamil and furosemide.

It is also possible to use combinations of active substances.

The amount of active substance, based on the solid drug form, may vary within wide limits depending on the activity and rate of release. Thus, the active substance content may be in the range from 0.1 to 90, preferably 0.5 to 60, % by weight.

Besides the active substances, the drug forms according to the invention contain as matrix-forming substances a) 10–99, preferably 40–95, % by weight of one or more water-soluble melt-processable homo- or copolymers of N-vinylpyrrolidone, b) 14 90, preferably 5–60, % by weight of a degraded starch, and c) 0–50% by weight of one or more conventional pharmaceutical auxiliaries, where the stated amounts are based on the total of the amounts of a), b) and, where appropriate, c).

Suitable as components a) are water-soluble melt-processable homo- or copolymers of N-vinylpyrrolidone or mixtures of such polymers. The polymers normally have glass transition temperatures in the range from 80 to 190, preferably 90 to 175, ° C. Examples of suitable homopolymers are polymers with Fikentscher K values in the range from 10 to 30. Suitable copolymers can contain as comonomers unsaturated carboxylic acids, eg. methacrylic acid, crotonic acid, maleic acid, itaconic acid, and esters thereof with alcohols having 1 to 12, preferably 1 to 8, carbon atoms, furthermore hydroxyethyl or hydroxypropyl acrylate and methacrylate, (meth)acrylamide, the anhydrides and monoesters of maleic acid and itaconic acid (the monoester preferably being formed only after the polymerization), N-vinylcaprolactam and vinyl propionate.

Preferred comonomers are acrylic acid and, particularly preferably, vinyl acetate. The comonomers may be present in amounts of from 20 to 70% by weight. The preparation of the polymeric components a) is generally known.

Water-soluble degraded starches (dextrins) are used as components b) according to the invention.

Dextrins of this type are commercially available and obtainable in a simple manner from starch by incomplete hydrolysis with dilute acid, by the action of heat or by oxidative or enzymatic degradation by amylases.

Starch degradation products obtainable by hydrolysis in aqueous phase and having a weight average molecular weight of from 2500 to 25,000 are usually referred to as saccharified starches, in distinction to the roasting dextrins, and are commercially obtainable as such.

Saccharified starches of this type differ chemically from the roasting dextrins inter alia in that on hydrolytic degradation in aqueus medium (normally suspensions or solutions), which is, as a rule, carried out with solids contents of from 10 to 30% by weight and preferably with acid or enzyme catalysis, there is essentially no possibility of recombination and branching, which is manifested not least also by other molecular weight distributions.

The preparation of saccharified starches is generally known and described, inter alia, in Günther Tegge, Stärke und Stärkederivate, Behr's Verlag, Hamburg 1984, page 173 and pages 220 et seq., and in EP-A 441 197. The saccharified starches to be used according to the invention are preferably those whose weight average molecular weight $M_w$ is in the range from 4000 to 16,000, particularly preferably in the range from 6500 to 13,000.

The starch degradation products have dextrose equivalents (DE) of from 2 to 40, preferably 2 to 30. The DE characterizes the reducing capacity based on the reducing capacity of anhydrous dextrose and is determined by the DIN 10 308 method, edition 5.71, of the Deutsche Normenausschuss Lebensmittel und landwirtschaftliche Produkte, (cf. also Günther Tegge, Stärke und St ärkederivate, Behr's Verlag, Hamburg 1984, page 305).

Particularly preferred components b) are the maltodextrins which have DE values in the range from 3 to 20, and starch degradation products with chain lengths of from 4 to 10 anhydroglucose units and with a high maltose content.

Suitable as components c) are conventional drugs aids such as, for example, fillers, lubricants, mold release agents, stabilizers, dyes, extenders or flow regulators, and mixtures thereof.

The active substances can be mixed with the matrix-forming components a) and b) and, where appropriate, components c) before or after the melting of the polymers. The mixing is preferably carried out in an extruder, preferably in a twin screw extruder or a single screw extruder with mixing compartment.

The active substance-containing melts are produced in the extruder at from 50 to 180, preferably 60 to 150, ° C. The still plastic extrudate is subsequently subjected to a continuous shaping, for example by the process described in EP-A 240 906 by passing the extrudate between two rolls which are driven in opposite directions and have mutually opposite depressions in the roll portion, with the shape of the depressions determining the shape of the tablets. Shaping by cold cutting is also suitable.

The melts are solvent-free, ie. the starting materials are not processed in the form of solutions, and neither water nor organic solvents are added.

Hot cutting is preferred. This entails the extrudates being pelletized immediately after emergence from the die arrangement on the extruder, for example by rotating knives or another suitable arrangement, expediently to pellets whose length is about the same as the diameter of the extrudate. These cut-off pellets are cooled in the stream of air or gas to such an extent that the surface is tack-free even before contact with other pellets or a vessel wall but, on the other hand, the pellets are still sufficiently plastic that they acquire a spherical shape through impacts, eg. with the wall of a subsequent cyclone. This results in a simple manner in pellets which are substantially spherical or lentil-shaped and have diameters of from 0.5 to 4, preferably 0.8 to 2, mm. The preferred smaller pellets are primarily suitable for filling capsules.

If required, the drug forms can also be provided with conventional coatings to improve the appearance or the taste.

Surprisingly, the addition of degraded starches synergistically increases the glass transition temperature of the polymer/starch mixture. The result of this is that, even on use of relatively low molecular weight polymers with correspondingly low glass transition temperatures, the phenomenon of cold flow is prevented. In addition, the degraded starches also promote rapid release of the active substance. It was also not to be expected that the degraded starches, which cannot be extruded as such without solvent and form no common phase with the polymers in aqueous solution, would show such good compatibility with the solvent-free polymer melts and lead to homogeneous mixtures.

EXAMPLES

The components were premixed in the ratios of amounts stated in the particular examples and introduced into the feed section of a twin screw extruder (Werner & Pfleiderer, ZSK 30). The melt extrusion took place with a product throughput of 3 to 4 kg/h. The temperatures in the individual zones ("sections") of the extruder and the temperature of the heated die strip is indicated in the experiments in each case. The die strip had 7 bores with a diameter of 1 mm. The extrudates emerging through the heated extruder die strip were pelletized by air-cooled hot-cut pelletizing (4 rotors, 400–850 rpm/min).

The release of active substance was measured by the USP XXI paddle method. This in vitro test method is used to determine the rate of dissolution of active substance-containing shaped articles, eg. tablets.

This was done by equilibrating 900 ml of a phosphate buffer with a pH of 6.8 and with the addition of 0.1% sodium lauryl sulfate in a 1 l round-bottom vessel to 37° C. A suitable amount of pellets (about 300 mg) in the size range from 1.25 to 1.60 mm was weighed in. The release of active substance from the pellets was determined in this USP XXI no change test at a paddle speed of 100 rpm by UV spectroscopy after 30 min in each case.

The starch degradation product used was a commercial maltodextrin (CPUR 1910 from Cerestar Deutschland GmbH) with an $M_{w\ of}$ 10540–12640 and a DE of 11–14.

The copolymer of 60% by weight vinylpyrrolidone and 40% by weight vinyl acetate used in Examples 2 to 4 had a K value of 30.

EXAMPLE 1

Temperatures of the extruder zones (sections 1–5) 20, 80, 140, 130, 130° C., temperature of extruder head 130° C., temperature of die strip 130° C.

| Active substance | Component a | Component b |
|---|---|---|
| Furosemide | Polyvinylpyrrolidone K value 17 | Maltodextrin |
| 20% by weight | 70% by weight | 10% by weight |
| Release after | 30 min 100% | |

EXAMPLE 2

Temperatures of the extruder zones (sections 1–5) 60, 120, 120, 110, 120° C., temperature of extruder head 130° C., temperature of die strip 120° C.

| Active substance | Component a | Component b |
|---|---|---|
| Nifedipine | Vinylpyrrolidone/ Vinyl acetate copolymer | Maltodextrin |
| 20% by weight | 75% by weight | 5% by weight |
| Release after | 30 min 80%. | |

EXAMPLE 3

Temperatures of the extruder zones (sections 1–5) 60, 120, 120, 120, 130° C., temperature of extruder head 130° C., temperature of die strip 160° C.

| Active substance | Component a | Component b |
|---|---|---|
| Ibuprofen | Vinylpyrrolidone/ vinyl acetate copolymer | Maltodextrin |
| 40% by weight | 50% by weight | 10% by weiqht |
| Release after | 30 min 80%. | |

EXAMPLE 4

Temperatures of the extruder zones (sections 1–5) 70, 130, 130, 140, 130° C., temperature of extruder head 130° C., temperature of die strip 160° C.

| Active substance | Component a | Component b |
|---|---|---|
| Captopril | Vinylpyrrolidone/ vinyl acetate copolymer | Maltodextrin |
| 20% by weight | 65% by weight | 15% by weight |
| Release after | 30 min 80%. | |

EXAMPLE 5

The glass transition temperatures of a polyvinylpyrrolidone with K value 17 and of the maltodextrin and of mixtures of the two components were measured (see table).

The glass transition temperatures were measured with a 912+thermal analyzer 990 DSC apparatus from TA Instruments. The temperature and enthalpy calibration took place in a conventional way. The sample weight was typically 13 mg. The samples were initially heated at 20 K/min to 190° C. and then rapidly cooled. The glass transition temperature (temperature of half the stage height of the glass stage in the heat flow curve) was found in the subsequent second heating run. By impressing a uniform previous thermal history, this measurement program makes a worthwhile comparison between the various samples possible. To determine the glass transition temperature, it is essential in the present case to comply with the stated temperature program.

Measurement by the DIN 53 765 method provides misleading values for the glass transition temperature because the samples are thermally damaged during the measurement procedure. The glass transition temperatures of the mixtures have also been calculated by the Gordon-Taylor equation used for polymer mixtures:

$$Tg=(w1Tg1+kw2Tg2)/(w1+kw2)$$

[M. Gordon, J. S. Taylor, Journal of Applied Chemistry USSR 2 (1952) 493; quoted by: H. A. Schneider, Polymer 30 (1989) 771]. w1 and Tg1 are the content by weight and the glass transition temperature, respectively, of component i. The fitting parameter k emerges as 0.37. The difference between the measured value and the fitted value is in the region of the measurement error (about 1 K).

It emerged from this that the Tg values measured in each case where higher than the calculated Tg values. It is evident from this that a synergistic increase in the Tg can be achieved by mixing components a) and b) (see table for results).

TABLE

| | PVP K17 | Maltodextrin content | | | |
|---|---|---|---|---|---|
| | 100% | 25% | 50% | 75% | 100% |
| Tg measured | 123° C. | 153° C. | 179° C. | 182° C. | 188° C. |
| Tg calculated | — | 138° C. | 156° C. | 172° C. | — |

EXAMPLE 6

Storage stability test:

A formulation was produced under the conditions stated in Example 3.

| Active substance | Component a | Component b |
|---|---|---|
| Ibuprofen | Polyvinylpyrrolidone | Maltodextrin |
| 20% by weight | K value 17 | 4% by weight |
| | 76% by weight | |

Release after 30 min 96.8%.

A formulation with the composition

| Active substance | Component a |
|---|---|
| Ibuprofen | Polyvinylpyrrolidone |
| 20% by weight | K value 17 |
| | 80% by weight |

showed 95% release after 30 min.

Both formulations were processed to bolus forms from the melt, and the release was determined by the USP XXI method.

The forms were stored in a closed vessel at a constant temperature of 50° C. for 4 weeks.

Subsequently only the formulation with maltodextrin showed no change in its consistency, whereas the formulation without maltodextrin was very tacky and showed partial flow, or the bolus forms were deformed.

We claim:

1. A solid drug form obtained by extruding of a solvent-free melt comprising, besides one or more active substances, a mixture of a) 10–99% by weight of one or more water-soluble, melt-processable, homo- or copolymers of N-vinylpyrrolidone, b) 1–90% by weight of degraded starches, and c) 0–50% by weight of one or more conventional pharmaceutical ancillary substances, and subsequent shaping.

2. A drug form as defined in claim 1, comprising maltodextrins as components b).

3. A drug form as defined in claim 1, having an active substance content of from 0.1 to 90% by weight.

4. A solid drug form as defined in claim 1, wherein component a) is present in an amount of 40–95% by weight and component b) is present in an amount of 5–60% by weight.

5. A solid drug form as defined in claim 4, wherein the active substance content is from 0.5 to 60% by weight.

* * * * *